United States Patent [19]

Tsou et al.

[11] Patent Number: 4,526,884

[45] Date of Patent: Jul. 2, 1985

[54] RUTHENIUM CONTAINING CATALYST COMPOSITION USEFUL FOR PROCESS FOR THE DEMERIZATION OF ACRYLIC COMPOUNDS

[75] Inventors: Dean T. Tsou, Solon; James D. Burrington, Richmond Hts.; Elizabeth A. Maher, University Hts.; Robert K. Grasselli, Chagrin Falls, all of Ohio

[73] Assignee: The Standard Oil Company, Cleveland, Ohio

[21] Appl. No.: 453,410

[22] Filed: Dec. 27, 1982

[51] Int. Cl.$^3$ .............................................. B01J 31/06
[52] U.S. Cl. ..................... 502/154; 502/159; 260/465.8 R; 564/160; 568/463; 568/461
[58] Field of Search .............................. 502/154, 159

[56] References Cited

U.S. PATENT DOCUMENTS

| | | | |
|---|---|---|---|
| 3,900,557 | 8/1975 | Strathdee | 502/159 X |
| 4,098,727 | 7/1978 | Haag et al. | 502/159 X |
| 4,179,403 | 12/1979 | Kim et al. | 502/159 |
| 4,323,698 | 4/1982 | Haag et al. | 502/159 X |
| 4,328,125 | 5/1982 | Drago et al. | 502/159 |

*Primary Examiner*—Patrick P. Garvin
*Attorney, Agent, or Firm*—Teresan W. Gilbert; Joseph G. Curatolo; Larry W. Evans

[57] ABSTRACT

Catalyst composition and process are provided for the dimerization of acrylic compounds. An acrylic compound may be dimerized in the liquid phase by contacting an acrylic compound with a catalyst in the presence of hydrogen, at a pressure of least about 1 psi and a temperature of at least about 50° C., wherein the catalyst comprises an organic polymer catalyst support, trivalent pendant atoms covalently bonded to the support, ruthenium complexed with said trivalent pendant atoms, and a second metal which is at least one of Pb and the Group VIII metals other than Ru and Pd and is disposed on the organic polymer catalyst support.

21 Claims, No Drawings

RUTHENIUM CONTAINING CATALYST COMPOSITION USEFUL FOR PROCESS FOR THE DEMERIZATION OF ACRYLIC COMPOUNDS

BACKGROUND OF THE INVENTION

The present invention relates to the liquid phase dimerization of acrylic compounds to form the corresponding dimers. More specifically, this invention relates to the dimerization of acrylic compounds using a catalyst comprising an organic polymer catalyst support covalently bonded to trivalent pendant atoms, ruthenium complexed with said trivalent pendant atoms, and a second metal selected from the group consisting of Pb and Group VIII metals other than Ru and Pd.

The dimerization of acrylic compounds has long been known. It has also long been known that ruthenium may catalyze the dimerization reaction. U.S. Pat. No. 3,729,498 to Masada, et al discloses the dimerization of acrylonitrile in the presence of a catalyst comprising ruthenium and at least one of bismuth, arsenic, phosphorous and antimony, which may be disposed on a carrier. U.S. Pat. No. 3,790,617, also to Masada, discloses a catalyst for vapor phase dimerization comprising ruthenium salts, which may be deposited on a support, such as active carbon, alumina, silica, silica-alumina, diatomaceous earth and pumice. The '617 patent further discloses that the activity of this catalyst may be enhanced by addition of an alkali metal hydroxide or a mixture of an organo-phosphorous compound combined with a halide of nickel, chromium, molybdenum or tungsten. U.S. Pat. No. 3,981,900 to Chabardes discloses a dimerization process using a catalyst comprising ruthenium which may be used as a solid ruthenium compound, as a finely divided ruthenium compound, in suspension or in solution. This catalyst may be promoted by a Group VIII metal or its oxide or hydroxide. This promoter may be deposited on a support or simply added to the reaction mixture. The promoters $Ru(OH)_3$, $RuO(OH)_2$ and $RuO_2$ are disclosed as being preferred.

Prior processes had the limitation of using catalysts which show poor conversion or inferior selectivity for the dimer over other undesirable by-products. This results in inefficient use of the acrylic feed and increased cost over a process using a catalyst exhibiting showing good conversion and selectivity for the dimer.

Previous dimerization processes also suffer from several limitations which are minimized or avoided by the process of the present invention. These limitations include homogeneity of the catalyst with the reaction mixture, making separation of the catalyst from the reaction mixture difficult and costly and catalyst recycling impracticable. Due to the fact that a large portion of the operating cost of a process is usually for the catalyst, this made prior processes expensive to perform.

In addition, previous processes used catalysts which, when supported, showed poor leaching characteristics. This resulted in a significant loss of the catalytic compounds to the reaction mixture thereby making recycling impracticable. This was a particularly significant limitation for ruthenium based catalysts due to the relatively high cost of ruthenium metal.

SUMMARY OF THE INVENTION

It is therefore an object of the present invention to provide a catalyst which is heterogeneous with respect to the reaction mixture, and to provide a liquid phase process for the dimerization of acrylic compounds by contacting an acrylic compound with a catalyst in the presence of hydrogen wherein the catalyst is heterogeneous with respect to the reaction mixture.

It is a further object of the present invention to provide a catalyst which shows good selectivity for dimerization, and to provide a process for the dimerization of acrylic compound by contacting an acrylic compound, in the presence of hydrogen, with a catalyst which shows good selectivity for the dimer.

These and other objects and advantages of the present invention are described in and become apparent from the specification which follows. The above and other objects and advantages are accomplished by the invention as hereinafter described and claimed.

In general, the process of the present invention includes contacting an acrylic compound with a catalyst in the presence of hydrogen, at a pressure of at least 1 psi and a temperature of at least 50° C., wherein the catalyst comprises an organic polymer catalyst support, trivalent pendant atoms covalently bonded to support, ruthenium complexed with the trivalent pendant atoms, and a second metal, wherein the second metal is selected from the group consisting of Pb, the Group VIII metals and mixtures thereof, other than Ru and Pd, and is disposed on the organic polymer catalyst support. The present invention is also directed to the catalyst described above.

DETAILED DESCRIPTION

Acrylic compounds may be defined as carboxyl or nitrile group containing organic compounds which have a double bond in a position "alpha" to the nitrile or carboxyl group. These compounds may be dimerized by the process of the present invention to form the corresponding dimers. Examples of compounds suitable for the present invention and their corresponding dimers are listed below in Table I. Other suitable acrylic compounds may include acrylic acid, methacrylic acid, the acrylates, such as methyl acrylate, ethyl acrylate and methyl methacrylate. This process is, however, especially preferred for the dimerization of acrylonitrile.

TABLE I

| Acrylic Compound | Dimer |
|---|---|
| acrylonitrile | dicyanobutene |
|  | adiponitrile |
| methacrylonitrile | 2,4-dimethyl-dicyanobutene |
|  | 2,4-dimethyl-dicyanobutane |
| acrylamide | adipamide |
|  | 2,3-dihydromuconamide |
| methacrylamide | 2,4-dimethyl-adipamide |
|  | 2.4-dimethyl-2,3-dihydromuconamide |
| acrolein | adipaldehyde |
|  | 2,3-dihydromuconaldehyde |
| methacrolein | 2,5-dimethyl-adipaldehyde |
|  | 2,5-dimethyl-2,3-dihydromuconaldehyde |

These dimers have several uses, including that of being precursers for the formation of polymers, including nylons. For example, the dimerization of acrylonitrile by the process of the present invention yields the linear dimers 1,4-dicyanobutane (adiponitrile) and 1,4-dicyanobutene, useful in making nylon 6,6.

The catalyst of the present invention comprises an organic polymer catalyst support, trivalent pendant atoms covalently bonded to the support, ruthenium (Ru) complexed with the trivalent pendant atoms, and a second metal which is disposed on the organic polymer catalyst support. This second metal is selected from the group consisting of lead (Pb) and Group VIII metals, other than Ru and palladium (Pd). Mixtures of these Group VIII metals metals may also be used as the second metal. In the process of the present invention the acrylic compound is contacted with this catalyst in the presence of hydrogen.

While any Group VIII metal other than Ru and Pd may be used as the second metal, it is preferred that the second metal be at least one of lead, cobalt (Co), iron (Fe) and nickel (Ni) since these metals are relatively less expensive than other appropriate metals and/or exhibit good conversion and selectivity characteristics. Lead is preferred as a second metal because it inhibits hydrogenation of the product dimer or the reactant acrylic compound to by-products. Both ruthenium and palladium are excluded from the pool of possible second metals. Ruthenium is excluded because the second metal should be a metal other than Ru. Palladium is excluded from the group of possible second metals because it does not exhibit superior conversion and selectivity properties when used in conjunction with ruthenium.

A wide variety of ruthenium complexes are suitable for the catalyst and process of the present invention. These complexes must be ones which are capable of catalyzing the dimerization reaction and capable of being disposed on an organic polymer catalyst support. In general these complexes include Ru complexes containing at least two complexing ligands which together have a total of at least four ligating bonds bonding to the ruthenium and are not covalently bonded to the support. Preferably these ligands are selected from the group consisting of halides, such as F, Cl, Br and I; water, carboxylic acids, such as acrylic acid, methacrylic acid, acetic acid and benzoic acid; aliphatic or aromatic carboxylic acid esters, such as benzyl acetate, methyl methacrylate, methacrylate and ethyl acetate; alcohols, such as methanol and ethanol; nitriles, such as acrylonitrile, acetonitrile and benzonitrile; aldehydes, such as acrolein and methacrolein; amides, such as acrylamide and glycols, such as ethylene glycol, or their derivatives; phosphines, such as triphenylphosphine; arsines, such as triphenylarsine and amines, such as triethylamine and ammonia, or mixtures thereof.

More preferably, however, the ruthenium is in the form of a complex represented by the formula:

$$RuL^1_a L^2_b L^3_c$$

wherein $L^1$ is a mono or bidentate ligand selected from F, Cl, Br, I, 2,4-pentanedionate, or mixtures thereof, wherein $L^2$ is one or more of acrylonitrile, methacrylonitrile, acetonitrile, propionitrile, benzonitrile, water and a group of the formula:

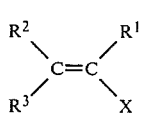

wherein X is CN, $CO_2R^4$, CHO or $CONR^4_2$ and $R^1$, $R^2$, $R^3$ and $R^4$ are independently selected from $C_{1-16}$ alkyl, $C_{1-16}$ aryl and H, wherein $L^3$ is $R^5_3P$, $R^5_3As$, $R^5_3Sb$, $R^6_3N$ and $R^6_2O$, or mixtures thereof wherein each $R^5$ is a $C_{1-16}$ group independently selected from alkyl, aryl, alkoxy, aryloxy, dialkylamino and diarylamino and $R^6$ is independently selected from $C_{1-16}$ alkyl, $C_{1-16}$ aryl or H, and further wherein a is 0 to 3;

b is 0 to 6;

c is 0 to 6; and a+b+c is at least 2 additionally and further selected so that $L^1$, $L^2$ and $L^3$ are additively bonded to the Ru with 4 to 6 ligating bonds.

Suitable Ru complexes include $RuCl_3.3H_2O$, $Ru(acac)_3$, $RuCl_2(AN)_3$, $RuBr_2(AN)_3$, $Ru(I)_2(AN)_3$, $RuCl_2(AN)_4$, $RuCl_2(CH_3CN)_3$, $RuCl_2(propionitrile)_3$, $RuCl_2(PhCN)_4$, $RuBr_2(AN)_4$, $RuI_2(AN)_4$, $RuCl_2(C_{12}H_{18})$, $RuCl_2(C_4H_8)_3$, $RuCl_2(C_8H_{12})_2$, $RuCl_2(C_8H_{12})$(p-toluidine), $Ru(stearate)_3$, $Ru(trifluoroacetylacetonate)_3$, $RuCl_3(AsPh_3)_2$, $RuCl_2(SbPh_3)_4$, $[Ru(NH_3)_5Br]Br_2$ and $[Ru(NH_3)_5I]I_2$, wherein "acac" is 2,4-pentanedionate, "AN" is acrylonitrile, and "Ph" is phenyl. $RuCl_3.3H_2O$, $Ru(acac)_3$, $RuCl_2(AN)_3$, $RuBr_2(AN)_3$, $Ru(I)_2(AN)_3$ are, however, especially preferred.

Ruthenium complexes suitable for use in the present invention are available commercially or may be prepared by procedures known in the art. Known procedures for producing suitable ruthenium complexes include refluxing a ruthenium hydrate with a ligand sought to be included in the ruthenium complex. For example, $RuCl_2(AN)_3$ may be prepared by refluxing $RuCl_3 3H_2O$ and acrylonitrile in ethanol.

Similarly, the second metal may exist as a wide variety of complexes. These complexes must be ones which are capable of promoting the dimerization reaction, compatible with the above described ruthenium complexes and capable of being disposed on organic polymer catalyst supports. In general, suitable complexes may be formed by complexing of the second metal with an organic or inorganic compound. Second metal complexes useful in the present invention are available from commercial sources. Examples of suitable complexes include $RhCl_3.3H_2O$, $OsCl_3.3H_2O$, $PtCl_4.5H_2O$, $CoCl_2.6H_2O$, $Co(acac)_2$, $Pb(OAc)_2$, $Ni(acac)_2$ and $Fe(OAc)_2$, wherein "OAc" is acetate ion. While not wishing to be bound by theory, it is hypothesized that at least some of the second metal disposed on the support is complexed with trivalent pendant atoms which are not complexed with the ruthenium.

The amount of ruthenium present in the process may vary widely. This amount, however, should be sufficiently great to catalyst the dimerization reaction. For this reason it is preferred that the Ru/acrylic compound molar ratio be at least about $10^{-4}$ and more preferably at least about $4 \times 10^{-4}$. Optimum conversion and economies are achieved at Ru/acrylic compound molar ratios of about $10^{-4}$ to $10^{-1}$, and more preferably about $4 \times 10^{-4}$ to $2 \times 10^{-3}$.

Although, consistent with the present invention, any amount of Ru may be present which can be deposited onto the organic polymer catalyst support, it is preferred that the catalyst be about 0.1 to 10 weight percent ruthenium. More preferably the catalyst is about 0.3 to 3 weight percent ruthenium.

The amount of the second metal used in the catalyst is determined in relation to the amount of ruthenium present, because the amount of second metal should be sufficient to promote the ruthenium in catalyzing the dimerization reaction without effectively competing with the ruthenium for the acrylic compound. In accordance with these considerations, it is preferred that the amount of the second metal present in the catalyst be such that the ratio by weight of ruthenium to the second metal is about 0.01–50. More preferably, however, the ratio of ruthenium to the second metal should be about 0.5–30.

Ruthenium and the second metal are disposed on the organic polymer catalyst support. The process and catalyst of the present invention are not limited to a particular support orgnic polymer material, except to the extent that the support is functionalized with trivalent pendant atoms. This polymer may be any of a number of known polymers, such as styrene divinylbenzene polymer, styrene acrylonitrile polymer, polyvinyl pyridine or other organic polymer in which trivalent pendant atoms can be incorporated. Most conveniently this polymer is a styrene polymer or copolymer in which the pendant atoms are covalently bonded to the phenyl moieties of the polymerized styrene monomers.

At least some of the pendant atoms covalently bonded to the organic polymer support complex with the ruthenium to strongly bond the ruthenium to the support. This stabilizes the ruthenium, thereby diminishing the tendency of Ru to be leached from the support and prolonging catalyst life and the catalyst's potential for recycling. Also, the formation of this Ru-trivalent pendant atom complex exerts an activating effect on the ruthenium resulting in greater activation of the ruthenium than when the ruthenium is complexed with trivalent atoms not covalently bonded to an organic polymer support. To this end, the pendant atoms should be capable of forming strong coordinate bonds with the ruthenium complex. P, As, Sb, Bi and N, when in the trivalent state, are preferred for this purpose. Phosphorus, however, is especially preferred. Mixtures of different pendant atoms may also be used.

As is appreciated by those skilled in the art, trivalent atoms, in order to be trivalent, must be bonded to other groups in addition to the substrate. The nature of these groups is not critical to the invention and may be alkyl, such as methyl or ethyl; aryl, such as phenyl; alkoxy, such methoxy or ethoxy; aryloxy, such as phenoxy; dialkylamino, such as dimethylamino; diarylamino, such as diphenylamino; and hydrogen. Although not necessary for the present invention, it is preferred that these groups contain no more than 12 carbon atoms.

Although amounts of catalyst should be present in the reaction mixture sufficient to provide good conversions of the acrylic compound, it is preferred that the molar ratio of the trivalent pendant atoms to the ruthenium in the catalyst not be greater than 20:1. It has been found that, in general, trivalent pendant atom/ruthenium ratios substantially in excess of 20:1 cause the catalyst to display diminished activity. It is further preferred that the trivalent pendant atom/ruthenium ratio be no greater than 10:1. However, in order to minimize alternative bonding patterns, it is preferred that the trivalent pendant atom/ruthenium ratio be at least 1:1.

When the pendant atoms are phosphorus it is preferred that the amount and distribution of phosphorus atoms in the polymer be such that the ruthenium atoms of the complex will not bond to two or more pendant phosphorus groups. Consequently, it is preferred that the pendant atoms be randomly distributed in the polymer at no more than 15 mole percent, and more preferably from 0.1 to 14 and even more preferably from 0.5 to 7 mole percent, based on the total number of polymerized monomeric units in the polymer backbone.

The catalyst may be prepared using any of several known techniques. These techniques include mixing the support with an excess of the Ru and ligands for a suitable period of time. Preferably this is performed in an inert atmosphere, and, if desired, in a suitable solvent, such as a ketone, alcohol or aromatic compound. A preferred technique includes adding the ruthenium and ligands in a solution to the support, either in batches or continuously, over an extended period of time. The second metal may be deposited onto the support simultaneously with the addition of the ruthenium, or may occur subsequent to, prior to or intermittently with respect to the Ru addition.

The present invention also contemplates the catalyst being optionally promoted with one or more substances in addition to the second metal. These promoters may be organic or inorganic bases, other than Group VA bases. It is preferred that the bases have a $pK_b$ of 0 to about 12. Bases suitable for this purpose include compounds such as N-methylpyrrolidine, triethylamine, sodium phenoxide, sodium carbonate, sodium cyanide, sodium thiophenol, and their potassium and cesium analogs. Organic bases such as N-methylpyrrolidine and triethylamine are, however, preferred. The molar ratio of base promoter to ruthenium and the second metal combined should be maintained at about 2 or more, and preferably at about 5 to about 50.

The process of the present invention may optionally be performed in the presence of any of several known solvents. Suitable solvents include ketones, alcohols, alkyl substituted or unsubstituted aromatics, ethers, organic nitriles and mixtures thereof. Acetone, methyl ethyl ketone, toluene, tetrahydrofuran, ethanol, and acetonitrile are, however, preferred. Dimethyl sulfoxide (DMSO) is not generally preferred as a solvent because its presence as a solvent tends to decrease catalyst effectiveness. In the situation where the reaction is not intended to go to equilibrium, products of the dimerization process may be used in the place of solvents. Excess amounts of the acrylic feeds may, however, be used instead of solvents, consistent with the present invention. The present invention may also be performed in the absence of a solvent or in the absence of an excess amount of a reactant or product.

The process of the present invention is carried out by contacting the acrylic compound with the catalyst for a suitable period of time. This time is determined by various factors, including the identity of the acrylic compound, the quantity of catalyst used and its composition, the temperature and pressure. The appropriate reaction time for a given set of conditions may readily be determined by one skilled in the art.

Usually the reaction is carried out at a temperature of about 50°–400° C. More preferably, however, this temperature is about 60°–200° C., and most preferably about 80°–150° C.

As is appreciated by those skilled in the art, hydrogen must be present in the reaction system. The pressure of the reaction system, exerted by hydrogen, is not critical to the present invention and may vary widely, with pressures on the order of about 1 to 1500 psi and preferably about 10 to 800 psi being suitable. Pressures of about 60–400 psi, however, are most preferred.

It is important to note that the process of the present invention may be practiced as either a batch or continuous process. The stability of the catalyst, however, makes it particularly suited for use in a continuous process.

Since the process of the present invention utilizes a catalyst which is heterogeneous to the reaction mixture, catalyst separation and recovery may be by conventional mechanical means, such as filtering, centrifugation or the like. Recovered catalyst may then be reprocessed or directly recycled, as is appropriate. The products may similarly be separated by conventional means, such as distillation or vacuum evaporation.

SPECIFIC EMBODIMENTS

Example 1 describes the preparation of a ruthenium-containing catalyst having a polymer support with pendant phosphorus atoms.

Example 1

Polymer preparation

A 20 percent cross-linked divinyl benzene para-diphenylphosphenostyrene polymer was prepared by the following method: styrene, 45 ml. and p-bromostyrene, 1.0 ml, were combined with 32 ml divinyl benzene and 75 ml toluene to form a styrene solution. The styrene solution was washed once with 50 ml of 1 percent NaOH and twice with 50 ml $H_2O$ per wash. The styrene solution was suspended in a solution of 5.4 g polyvinyl alcohol in 800 ml of water, to which 0.68 g of azobisisobutyrylnitrile were added. The combination was flushed with nitrogen, and then heated to and maintained at 80° C. for 5 hours with constant stirring. The polymer was recovered by filtration, washed with water and extracted with acetone continuously for 12 to 16 hours. The resulting polymer beads were dried under vacuum for 8 hours, and resulted in a total yield of 69.2 g.

The para-bromine substituted polystyrene beads, 20 g obtained by the above method were suspended in 100 ml toluene at 60° C. for 1 hour. The suspension was then flushed with nitrogen and a nitrogen atmosphere maintained. Five milliliters of BuLi, (1.55M) in hexane, was added to the suspension. The resulting reaction mixture was then stirred 2 hours at 60° C. under nitrogen. The excess toluene was then removed. Fifty milliliters of tetrohydrofuran (THF), and 1.7 ml of diphenylchlorophosphine were then added. The reaction mixture was stirred at 60° C. for two more hours, after which the polymer beads were filtered and washed with THF, THF-$H_2O$, $H_2O$, THF-$H_2O$ and finally THF. The beads were extracted with acetone continuously for 4 hours under nitrogen, and dried under vacuum for 12 to 16 hours. Analysis disclosed the beads comprising a bromine substituted styrene divinyl benzene copolymer with P substitution.

Ruthenium/Second Metal Addition

A slurry was formed of 1.0 gm of the divinylbenzene para-diphenylphosphenostyrene polymer and 62.8 mg $RuCl_3.3H_2O$ and 57.1 mg of $CoCl_2.6H_2O$ in 2 ml methanol. The slurry was flushed with $N_2$ and stirred at room temperature. The catalyst slurry was then filtered and washed with methanol until the filtrate was colorless. The residue was then dried by evaporation and placed under a vacuum for 15 minutes. This produced a catalyst which was 0.23 percent by weight ruthenium, and had a Ru/Co weight ratio of 27.

The experiments in Examples 2 through 9 were performed to demonstrate various aspects of the invention by testing for the dimerization of acrylonitrile. It is apparent from these examples that the percent Ru and percent second metal in the catalyst may vary over a wide range, consistent with the present invention. The catalyst in Examples 2 through 9 had a styrene/divinyl benzene polymer support with pendant phosphorus atoms, prepared as in the section entitled "Polymer Preparation" in Example 1. These experiments were performed by placing 0.5 gm of catalyst, 7 ml of acrylonitrile, 0.4 ml N-methylpyrrolidine, 20 ml of acetone and 1 ml $C_{15}H_{32}$, as an internal standard for gas chromatography, in a 300 ml Parr autoclave with a glass liner. The autoclave was sealed and purged with $H_2$, then pressurized to a hydrogen pressure of 80 psi and heated to 110° C. for 3 hours. The mixture was then removed from the autoclave, filtered to separate the catalyst, and subjected to analysis by gas chromatography.

The results of the experiments in Examples 2 through 9 are represented in Tables II and III. In these tables, percent ruthenium and percent M represent the weight percent of ruthenium and the second metal, respectively, in the ruthenium and second metal containing supported catalyst. "PN" denotes propionitrile. "M" denotes the second metal. The heading "dimer" denotes 1,4-dicyanobutenes plus adiponitrile. Percent conversion and selectivity were calculated as follows:

$$\text{Percent Yield } PN = \frac{\text{Moles } PN}{\text{Moles } AN \text{ Fed}} \times 100$$

$$\text{Percent Yield Dimer} = \frac{2 \times \text{Moles Dimer}}{\text{Moles } AN \text{ Fed}} \times 100$$

Percent Conversion =

$$\frac{\text{Moles } AN \text{ fed} - \text{moles } AN \text{ recovered}}{\text{Moles } AN \text{ fed}} \times 100$$

$$\text{Selectivity} = \frac{\text{Percent Yield Specific Product}}{\text{Percent Yield } PN + \text{Percent Yield Dimer}} \times 100$$

The experiments in comparative Examples 2 and 4 were performed using catalysts comprising ruthenium complexed to phosphine groups covalently bonded to a styrene/divinyl benzene support prepared as in Example 1. Examples 3, 5, 6 and 7 were performed using catalysts analogous to those in Examples 2 and 4, respectively, except that they included cobalt as a second metal in addition to ruthenium. The results of these experiments are indicated in Table II and demonstrate the superior selectivity for the dimer exhibited by the present invention wherein the catalyst contains a second metal in addition to ruthenium.

TABLE II

| | | | | | | | Selectivity | |
|---|---|---|---|---|---|---|---|---|
| Ex | Catalyst | Ru | Ru/P | M | Ru/M | Conv. | PN | Dimer |
| 2 | $RuCl_3 3H_2O$ | 0.44 | 0.11 | — | — | 38 | 71 | 29 |
| 3 | $RuCl_3 3H_2O$—$CoCl_2 6H_2O$ | 0.23 | 0.054 | 0.005 | 27.0 | 32 | 50 | 50 |
| 4 | $RuCl_2(AN)_3$ | 1.2 | 0.26 | — | — | 48 | 59 | 41 |
| 5 | $RuCl_2(AN)_3$—$Co(acac)_2$ | 1.7 | 0.42 | 0.57 | 1.7 | 25 | 46 | 54 |
| 6 | $Co(acac)_2 RuCl_2(AN)_3$ | 0.61 | 0.12 | 0.19 | 1.7 | 76 | 64 | 36 |

TABLE II-continued

| Ex | Catalyst | Ru | Ru/P | M | Ru/M | Conv. | Selectivity PN | Dimer |
|---|---|---|---|---|---|---|---|---|
| 7 | RuCl$_2$(AN)$_3$Co(acac)$_2$ | 0.67 | 0.16 | 0.69 | 0.57 | 43 | 49 | 51 |

Comparative Example 8 was performed to demonstrate that the increased conversion and selectivity obtained using the process of the present invention is due to both ruthenium and the second metal being present in the catalyst of the present invention, not due to the second metal independently catalyzing the reaction. The results of this experiment are indicated below in Table III.

Example 9, the results of which are also indicated in Table III, was performed to demonstrate the utility of lead in the catalyst and process of the present invention.

TABLE III

| Ex | Catalyst | Ru | Ru/P | M | Ru/M | Conv. | Selectivity PN | Dimer |
|---|---|---|---|---|---|---|---|---|
| C8 | Co(acac)$_2$ | — | — | 0.45 | — | 10 | 100 | — |
| 9 | RuCl$_2$(AN)$_3$—Pb(OAc)$_2$ | 2.6 | 0.61 | 3.4 | 1.6 | 53 | 46 | 54 |

The above Examples were performed to demonstrate that superior conversion of acrylic compounds and selectivity for the dimer may be obtained using the process and catalyst of the present invention. It is to be understood, however, that the invention is not to be limited by the examples. Selection of specific second metals, promoter ligands, promoter bases, solvents, reaction conditions and ratios can be determined by the total specification disclosure provided herein, without departing from the spirit and scope of the invention herein disclosed and described. The scope of the invention, including equivalent embodiments, modifications and variations, is to be determined by the scope of the following claims.

We claim:
1. A catalyst composition comprising an organic polymer catalyst support, trivalent pendant atoms covalently bonded to the support, ruthenium complexed with said trivalent pendant atoms, and a second metal, wherein the second metal is at least one of Pb, Co, Fe and Ni and is disposed on the organic polymer catalyst support.

2. The catalyst of claim 1 wherein the ruthenium is complexed with at least one of water, a halide, a carboxylic acid, an aliphtic or aromatic carboxylic acid ester, an alcohol, a nitrile, an aldehyde, an amide, a glycol, a phosphine, an arsine, an amine and ammonia.

3. The catalyst of claim 1 wherein the ruthenium is in the form of a complex represented by the formula:

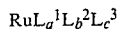

wherein
L$^1$ is a mono or bidentate ligand selected from F, Cl, Br, I, 2,4-pentanedionate, or mixtures thereof,
wherein
L$^2$ is one or more of acrylonitrile, methacrylonitrile, acetonitrile, propionitrile, benzonitrile, water and a group of the formula:

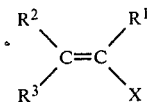

wherein X is CN, CO$_2$R$^4$, CHO or CONR$_2^4$ and R$^1$, R$^2$, R$^3$ and R$^4$ are independently selected from C$_{1-16}$ alkyl, C$_{1-16}$ aryl and H;
wherein
L$^3$ is R$_3^5$P, R$_3^5$As, R$_3^5$Sb, R$_3^6$N and R$_2^6$O, or mixtures thereof wherein each R$^5$ is a C$_{1-16}$ group independently selected from alkyl, aryl, alkoxy, aryloxy, dialkylamino and diarylamino and R$^6$ is independently selected from C$_{1-16}$ alkyl, C$_{1-16}$ aryl or H;
and
wherein
a is 0 to 3;
b is 0 to 6;
c is 0 to 6; and
a+b+c is at least 2; and
wherein
L$^1$, L$^2$ and L$^3$ are additively bonded to the Ru with 4 to 6 ligating bonds.

4. The catalyst of claim 1 wherein the catalyst is about 0.1 to 10 weight percent ruthenium.

5. The catalyst of claim 4 wherein the catalyst is about 0.3 to 3 weight percent ruthenium.

6. The catalyst of claim 1 wherein the ratio by weight of ruthenium to the second metal is about 0.01-50.

7. The catalyst of claim 6 wherein the ratio by weight of ruthenium to the second metal is about 0.5-30.

8. The catalyst of claim 1 wherein the molar ratio of the trivalent pendant atoms to the ruthenium is equal to or less than 20:1.

9. The catalyst of claim 8 wherein the molar ratio is about 10:1 to about 1:1.

10. The catalyst of claim 1 wherein the trivalent pendant atoms are selected from the group consisting of P, As, Sb, Bi, N and mixtures thereof.

11. The catalyst of claim 10 wherein the trivalent pendant atoms comprise phosphorus.

12. The catalyst of claim 1 wherein the polymer is selected from the group consisting of styrene/divinyl benzene polymers, styrene acrylonitrile polymers, polyvinyl pyridine polymers and mixtures thereof.

13. A catalyst composition for acrylic compound dimerization comprising an organic polymer catalyst support, trivalent pendant atoms covalently bonded to the support wherein the trivalent pendant atoms are selected from the group consisting of P, As, Sb, Bi and N, a second metal which is selected from the group consisting of Pb, Co, Fe and Ni and is disposed on the organic polymer catalyst support, and ruthenium, wherein the ruthenium is complexed with the trivalent pendant atoms and is in the form of a complex represented by the formula:

$$RuL^1_a L^2_b L^3_c$$

wherein
   $L^1$ is a mono or bidentate ligand selected from F, Cl, Br, I, 2,4-pentanedionate, or mixtures thereof,
wherein
   $L^2$ is one or more of acrylonitrile, methacrylonitrile, acetonitrile, propionitrile, benzonitrile, water and a group of the formula:

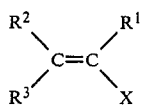

wherein X is CN, $CO_2R^4$, CHO or $CONR^4_2$ and $R^1$, $R^2$, $R^3$ and $R^4$ are independently selected from $C_{1-16}$ alkyl, $C_{1-16}$ aryl and H;
wherein
   $L^3$ is $R^5_3P$, $R^5_3As$, $R^5_3Sb$, $R^6_3N$ and $R^6_2O$, or mixtures thereof wherein each $R^5$ is a $C_{1-16}$ group independently selected from alkyl, aryl, alkoxy, aryloxy, dialkylamino and diarylamino and $R^6$ is independently selected from $C_{1-16}$ alkyl, $C_{1-16}$ aryl or H; and wherein
   a is 0 to 3;
   b is 0 to 6;
   c is 0 to 6; and
   a+b+c is at least 2; and
wherein
   $L^1$, $L^2$ and $L^3$ are additively bonded to the Ru with 4 to 6 ligating bonds
wherein the catalyst is about 0.1 to 10 weight percent ruthenium, the ratio by weight of ruthenium to the second metal is about 0.01–50, and the molar ratio of the trivalent pendant atoms to the ruthenium is about 20:1 or less.

14. The catalyst of claim 1 wherein the second metal is cobalt.

15. The catalyst of claim 1 wherein the second metal is nickle.

16. The catalyst of claim 1 wherein the second metal is iron.

17. The catalyst of claim 1 wherein the second metal is lead.

18. The catalyst of claim 3 wherein the second metal is cobalt.

19. The catalyst of claim 3 wherein the second metal is nickle.

20. The catalyst of claim 3 wherein the second metal is iron.

21. The catalyst of claim 3 wherein the second metal is lead.

* * * * *